United States Patent

Fried

[11] 4,219,647
[45] Aug. 26, 1980

[54] CERTAIN AMIDES OF PROSTACYCLIN AND RELATED COMPOUNDS

[76] Inventor: Josef Fried, 5715 S. Kenwood Ave., Chicago, Ill. 60636

[21] Appl. No.: 835,731

[22] Filed: Sep. 22, 1977

Related U.S. Application Data

[63] Continuation-in-part of Ser. No. 803,747, Jun. 6, 1977.

[51] Int. Cl.² .................................................. C07D 307/93
[52] U.S. Cl. ................................... 542/421; 542/430;
260/346.22; 260/346.73
[58] Field of Search ....................... 260/346.22, 346.73;
542/421, 430

[56] References Cited

FOREIGN PATENT DOCUMENTS 851122 8/1977 Belgium .

OTHER PUBLICATIONS

Johnson et al., J. Am. Chem. Soc. 99 (12)Jun. 8, 1977, pp. 4182–4184.

*Primary Examiner*—Henry R. Jiles
*Assistant Examiner*—Bernard Dentz
*Attorney, Agent, or Firm*—Lawrence Rosen; Berry E. Janet

[57] ABSTRACT

This invention relates to compounds of the formula:

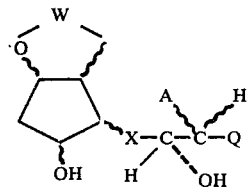

wherein
A is hydrogen or fluorine;
Q is alkyl or alkenyl of from 3 to 6 carbon atoms;
X is C=C or C≡C
W is

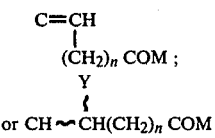

wherein
n is an integer of from 2 to 5;
Y is halogen; and
M is higher alkoxy; an amino acid radical; or an amino acid alkyl ester radical.

The compounds of the invention are physiologically active and are useful in increasing blood flow and lowering blood pressure which are properties desirable for hypotensive agents.

2 Claims, No Drawings

CERTAIN AMIDES OF PROSTACYCLIN AND RELATED COMPOUNDS

This application is a continuation in part application of my copending previously filed application Ser. No. 803,747 filed June 6, 1977, said prior filed application incorporated herein by reference.

This invention relates to and has as its objectives the production of compounds of the following formula,

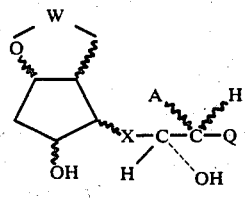

wherein
A is hydrogen or fluorine;
Q is alkyl or alkenyl of from 3 to 6 carbon atoms;
X is C=C or C≡C
W is

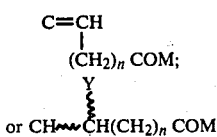

wherein
n is an integer of from 2 to 5;
Y is halogen; and
M is higher alkoxy; an amino acid radical; or an amino acid alkyl ester radical.

More particularly, this invention relates to compounds of the formulae,

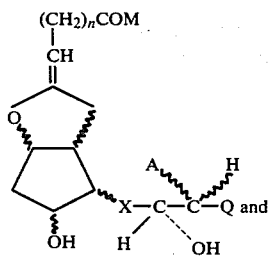

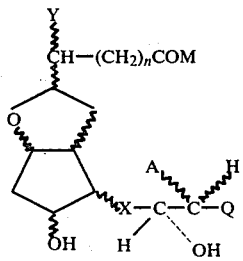

wherein X, A, Q, M and n are as hereinbefore defined.

In its most preferable embodiment of the instant invention, it has been found that most satisfactory results are obtained with the compounds of this invention wherein A is hydrogen or fluorine; Q is an alkyl group of from 3 to 6 carbon atoms; n is an integer from 2 to 5; Y is bromine, and M is higher alkoxy for example, an alkoxy moiety of more than 8 carbon atoms; or an amino acid radical or an amino acid ester radical, preferably an alkyl ester of amino acid radical.

Whenever in the formulae set forth in this specification and the claims appended hereto, a curved line ( $\xi$ ) is employed in the linkage of atoms, it is meant to denote that the connected atoms may either be in the alpha- or beta- position, that is, either above or below the plane of the paper as may be determined in each of the respective compounds involved.

The amino acid and amino acid ester radicals of this invention are those which are preferably obtained from amino acids or amino acid esters such as glycine, taurine, leucine, phenylalanine, proline, histidine or alanine and the esters thereof, for example, the alkyl esters thereof, such as methyl or ethyl glycinate, ethyl leucinate and the like; all as well known to and recognized by the skilled worker in the art.

The final products of this invention are physiologically active compounds possessing prostacyclin-like activity. Thus, the final products of this invention possess the ability to cause an increase in blood flow and lowering of blood pressure and may therefore be useful as hypotensive agents to treat various hypertensive states.

In addition, the products of this invention are inhibitors of platelet aggregation and may therefore be useful in the treatment of myocardial infarcts, postoperative thrombosis and atheroschlerosis.

Moreover, some of the products of this invention have been found to be resistant to the action of the major prostacyclin inactivating enzyme, the 15-hydroxyprostaglandin dehydrogenase, thereby producing or enhancing the action of these substances when compared with naturally occurring prostacyclin.

The pharmacologically active compounds of this invention may be administered to the patient or animal being treated therewith in any manner known and convenient to the skilled worker practicing the invention. The dosage and concentration of the final product may be adjusted to the requirements of the patient and the properties of the respective compounds being employed. The skilled worker may prepare the final products in such compositions and dosage forms as are usually required for such purposes depending upon the route of administration selected for the ultimate composition, for example, parenteral, peroral, or topical final dosage forms and routes of administration.

The final products of this invention are prepared by the processes of this invention which entail a number of steps beginning with certain 13-dehydroprostacylin salts which are the subject of my previous filed U.S. patent application, Ser. No. 803,747 filed on June 6, 1977, as well as certain prostacyclin salts described by Johnson et al, in Vol. 12, Prostaglandins, page 915 (1976).

The final compounds of this invention, wherein M is higher alkoxy, for example, an alkoxy moiety having eight carbon atoms or more, may be prepared in accordance with the process of this invention. The corresponding prostacyclin salts, for example, 13-dehydroprostacyclin sodium salt, and such other prostacyclin salts may be obtained in accordance with the teachings of my prior filed copending application Ser. No. 803,747, filed June 6, 1977, and more particularly Examples 8, 9 and 10 thereof, may be treated with a suitable alkylating agent, for example, a halo-alkane, such as a higher primary or secondary haloalkane, such as an iodoalkane having from 8 to 18 carbon atoms, for example, iodododecane, iodododecane, or a cyclic haloalkane, for example, an iodocycloalkane, for example, iodocyclooctane, iodocyclohexane or 5-cyclopentano-1-iodo-n-pentane, to yield the desired higher alkyl ester of the respective prostacyclin starting material.

The final compounds of this invention wherein M is an amino acid or amino acid ester radical, may be prepared in accordance with the process of this invention. The halo ether prostacyclin derivatives as may be obtained in accordance with the teachings of my prior filed copending application Ser. No. 803,747, filed June 6, 1977, and more particularly as set forth in Examples 1 and 2 thereof, may be first reacted with a carbonyl diimidazole to form a corresponding acyl imidazolide, which is also a new compound of this invention. The resultant acyl immidazolide compound is then reacted with the desired acid ester or salt to form the corresponding carboxamide compounds, which are also new compounds of this invention. In addition to the foregoing, the final compounds of this invention possessing a double bond in the 13,14 position, i.e. wherein A is C=C, may also be prepared in accordance with the process of this invention. The 13,14 double bond starting materials corresponding to those bromo ethers set forth in my copending prior filed application, Ser. No. 803,747, have been described by Corey et al in Vol. 99, Journal of the American Chemical Society, page 2006 (1977) and may be treated in accordance with the aforementioned process to obtain the desired corresponding carboxamide compounds, which are also new compounds of this invention.

The carboxamide compounds thus obtained may then be further treated in accordance with the process of this invention to obtain the desired prostacyclin amide final products. The carboxamide compounds are then dehydrohalogenated as by treatment with a strong organic base, for example, potassium t-butoxide, 1,5-diazabcyclo [5.4.0] undec-1-ene (DBU) or other strong base, to yield further new prostacyclin amides of this invention..

While the foregoing represents a general description of the processes and products of this invention, it should be clearly understood by the skilled worker that the substitution of various equivalent starting materials or reactants for those specifically set forth herein in the foregoing equations and subsequent examples will yield equivalent results. Thus, where in the equations set forth hereinabove, when the M and W moieties are varied by the skilled worker, equivalent results and corresponding end products will be obtained by the practice of this invention.

This invention may be further illustrated by the following examples:

EXAMPLE 1

13-Dehydroprostacyclin Dodecyl Ester

To a solution of 37.7 mg (0.1 mmol) of 13-dehydroprostacyclin sodium salt in 2 ml of DMF is added 30 mg of 1-iodododecane (0.1 mmol) and the solution allowed to stir at room temperature for 18 hours. At the end of this period the solution is added to ice water and the organic material extracted with methylene chloride. The methylene chloride extract is back-washed twice with water, dried over sodium sulfate and the solvent removed in vacuo. The material is then dried in high vacuum. The residue represents the dodecyl ester of 13-dehydroprostacyclin. Similarly, following the foregoing procedure, but substituting an equivalent amount of iodocyclooctane and iodododecane for the iodododecane, the respective cyclooctane and decane esters are obtained.

EXAMPLE 2

(5R,6R)-9-deoxy-5-bromo-6,9α-epoxy-13-dehydro-PGF$_{1α}$ Glycine Methyl Ester A solution of 249 mg (0.58 mmole) of (5R,6R)-9-deoxy-5-bromo-6,9α-epoxy-13-dehydro-PGF$_{1α}$ and 100 mg (0.58 mmole) of carbonyl diimidazole in 4 ml of dry tetrahydrofuran are allowed to react for a half hour. At the end of that period 52 mg (0.58 mmole) of methyl glycinate is added. The solution is allowed to remain at room temperature overnight and the solvent removed in vacuo. The residue is taken up in dilute hydrochloric acid and methylene chloride and the methylene chloride extract washed twice with water. On evaporation of the solvent in vacuo there remains (5R,6R)-9-deoxy-5-bromo-6,9α-epoxy-13-dehydro-PFG$_{1α}$glycine methyl ester. Similarly, following the foregoing procedure but substituting an equivalent amount of methyl phenylalaninate or methyl leucinate for the methyl glycinate, the corresponding amide derivatives are obtained.

EXAMPLE 3

13-Dehydroprostacyclin Glycine Methyl Ester

A mixture of 50 mg (0.1 mM) of the glycine methyl ester obtained in Example 2 above, and 61 mg (0.4 mM) of DBU is diluted with 0.30 ml of toluene, degassed with $N_2$, and immersed in a 98–100 degrees oil bath for 2 hours. The solution is diluted with 0.50 ml 4:1 hexane/ethylacetate and the resulting precipitate washed with two 0.25 ml portions of the same solvent. The combined extracts are washed rapidly with two 1 ml portions of cold NaCl-saturated 0.1 N HCl, dried over $Na_2SO_4$, and concentrated under nitrogen to yield 13-dehydroprostacyclin glycine methyl ester.

The invention may be variously otherwise embodied within the scope of the appended claims.

What is claimed is:

1. A compound of the formula:

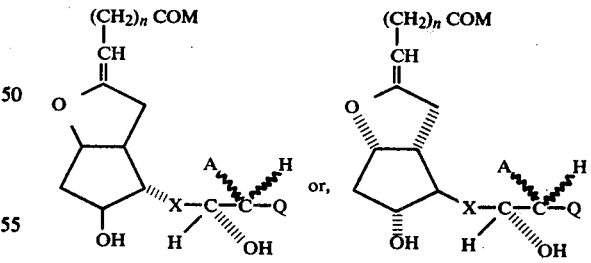

wherein
X is C=C or C≡C;
A is F or H;
Q is alkyl or alkenyl of 3 to 6 carbon atoms;
n is an integer of from 2 to 5; and
M is an amino acid radical; or an amino acid aklyl ester radical, said radicals being derived from amino acids selected from the group consisting of glycine, taurine, leucine, phenylalanine, proline, histidine and alanine.

2. A compound of the formula,

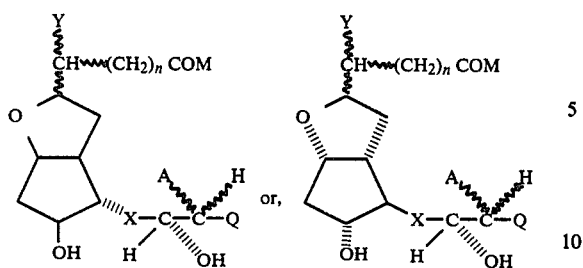
wherein
Y is halo; and
X, A, Q, n, and M are as defined in claim 1.
* * * * *